United States Patent

Stanley et al.

[11] Patent Number: 5,861,250
[45] Date of Patent: Jan. 19, 1999

[54] PROTECTING NUCLEIC ACIDS AND METHODS OF ANALYSIS

[75] Inventors: Christopher John Stanley, Huntingdon, Great Britain; Henrik Orum, Vaerlose, Denmark; Mikkell Jorgensen, Glostrup, Denmark; Ole Basboll, Birkerod, Denmark

[73] Assignee: PNA Diagnostics A/S, Copenhagen, Denmark

[21] Appl. No.: 659,529

[22] Filed: Jun. 6, 1996

[51] Int. Cl.⁶ .......................... C12P 19/34; C07H 21/00; C12N 15/00

[52] U.S. Cl. .......................... 435/6; 435/91.2; 435/91.1; 536/25.32; 536/17.3; 935/77; 935/78

[58] Field of Search .......................... 435/6, 91.2, 91.1; 536/25.32, 17.3; 935/77, 78

[56] References Cited

U.S. PATENT DOCUMENTS

| | | | |
|---|---|---|---|
| 4,800,159 | 1/1989 | Mullis et al. | 435/172.3 |
| 5,539,082 | 7/1996 | Nielsen et al. | 530/300 |
| 5,578,468 | 11/1996 | Pickup et al. | 435/91.32 |

FOREIGN PATENT DOCUMENTS

92/20703   11/1992   WIPO.

*Primary Examiner*—Kenneth R. Horlick
*Assistant Examiner*—Joyce Tung
*Attorney, Agent, or Firm*—Nikaido Marmelstein Murray & Oram, LLP

[57] ABSTRACT

A selected region of a nucleic acid is protected from attach by nuclease by completing to the nucleic acid a nucleic acid analogue of the PNA type. The surviving sequence may be detected in an assay, optionally after amplification. A PCR reaction may be sterilized and its product assayed by protecting a characterizing region of the product by PNA hybridization followed by nuclease degradation of unprotected nucleic acid.

23 Claims, 1 Drawing Sheet

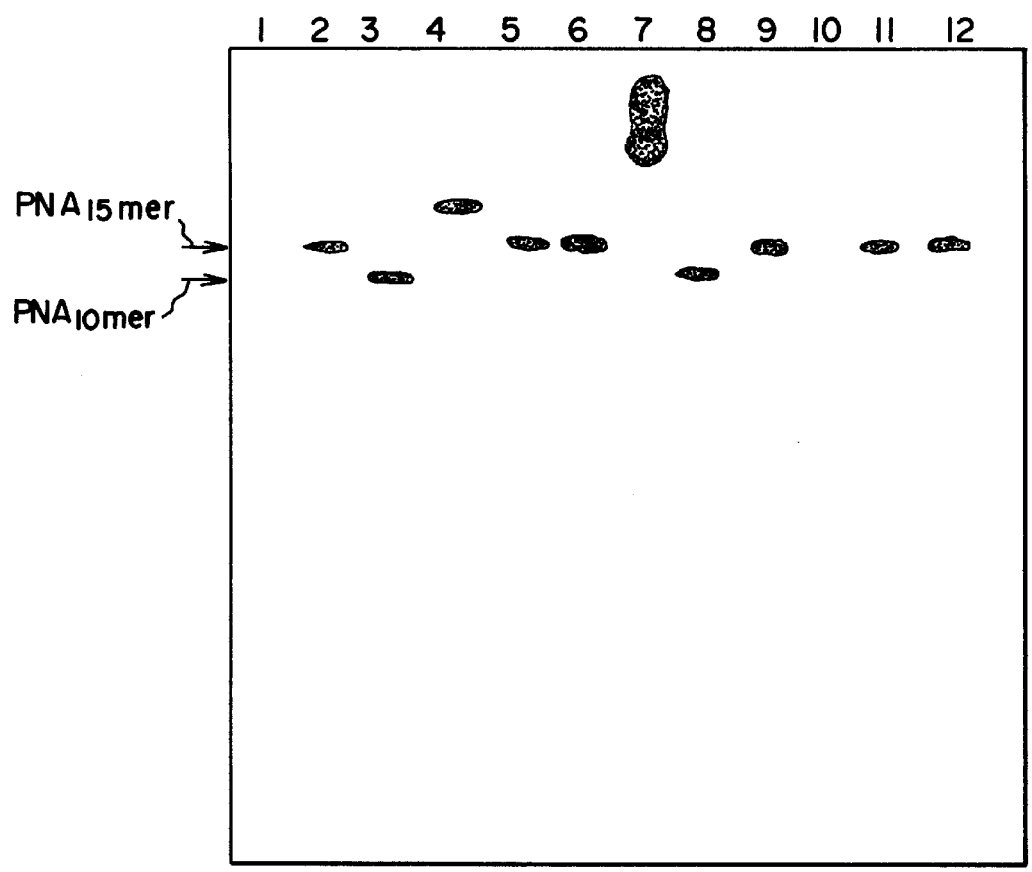

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

TGTACGTCAC AACTA 15

( 2 ) INFORMATION FOR SEQ ID NO:2:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Leu Arg Arg Ala Ser Leu Gly 7
1               5

( 2 ) INFORMATION FOR SEQ ID NO:3:

( i ) SEQUENCE CHARACTERISTICS:
( A ) LENGTH: 40 base pairs
( B ) TYPE: nucleic acid
( C ) STRANDEDNESS: single -continued (D) TOPOLOGY: linear (ii) MOLECULE TYPE: DNA (xi) SEQUENCE DESCRIPTION: SEQ ID NO:3:

CTAGAGGATC TAGTTGTGAC GTACAGGATC TTTTTCATAG                    40

(2) INFORMATION FOR SEQ ID NO:4:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:4:

TAGTTGCGAC GTACA                                                15

(2) INFORMATION FOR SEQ ID NO:5:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:5:

TGTACGTCAC AACTA                                                15

PROTECTING NUCLEIC ACIDS AND METHODS OF ANALYSIS

CROSS REFERENCE TO RELATED APPICATION

This application is a continuation-in-part of International Application PCT/EP94/03973, filed Nov. 30, 1994, and designating the U.S.

The present invention relates to methods of protecting nucleic acids from attack, eg. by nucleases, and analytical methods and in particular to methods for detecting the presence in a nucleic acid containing sample of a sequence of interest.

At present the usual way of determining whether a particular base sequence is present in a sample of nucleic acid is filter hybridisation. The nucleic acid is extracted from starting materials and purified. It may need to be amplified by a process such as PCR. The nucleic acid is then immobilised in single stranded form on a filter and is probed with a labelled oligonucleotide having a sequence complementary to that which is to be detected. Before being immobilised, the nucleic acid may be run on a gel to separate different molecular weight nucleic acid fragments. This is the widely used Southern blot procedure. This procedure has numerous drawbacks. The nucleic acid needs to be separated from other materials. Where the nucleic acid is DNA, it will normally be necessary to go through a denaturation step. The stringency conditions of the hybridisation will need careful adjustment to avoid false positives and to achieve the desired level of discrimination between similar sequences. Because of the limited signal to noise of the filter hybridisation, amplification steps will often be necessary to produce sufficient of the sequence of interest for detection. This generates many opportunities for the production of false negatives.

Nucleic acid analogues having important new utilities in assay procedures and in the field of diagnostics have been described in WO 92/20703. These nucleic acid analogues had a number of new properties making them of special importance in the field of diagnostics as well as in the field of antisense therapeutics. Such nucleic acid analogues are referred to herein as "PNAs".

They typically feature a polyamide backbone bearing a sequence of ligands which are nucleic acid bases. The analogues described there have the property of hybridising with great specificity and stability to natural nucleic acids of complementary sequence.

We have now discovered that such nucleic acid analogues have the further valuable property of protecting sequences of single stranded nucleic acids to which they are hybridised from being degraded by certain reagents under circumstances and conditions in which the reagents would normally be effective to produce degradation of said single stranded nucleic acids. Regions of the nucleic acid not hybridised to the nucleic acid analogue may be degraded as normal.

Accordingly, the present invention provides a method of protecting a selected region of a nucleic acid from attack by a reagent, which method comprises forming a complex between the nucleic acid and a nucleic acid analogue which hybridises thereto in a sequence selective manner and exposing said nucleic acid to a nucleic acid attacking reagent, wherein said complex is more stable against attack by said reagent than said starting nucleic acid.

The nucleic acid may be RNA or DNA.

Preferably, said reagent is a nuclease and is capable of degrading said nucleic acid either completely or by cleaving it at certain locations.

In the most straightforward case, the selected region of the nucleic acid to be protected will be constituted by the nucleic acid sequence to which the nucleic acid analogue hybridises. However, where the attacking reagent is an exonuclease capable of degrading nucleic acids under the conditions used only by working in from the 5' and 3' ends, a larger selected region may be protected by placing a respective nucleic acid analogue at each end of the selected region leaving part of the selected region unhybridised between the two nucleic acid analogue sequences. The intervening part of the selected region is fenced off from access by the exonuclease. Where the exonuclease is, under the conditions employed, able only to attack from the 5' or 3' end, a single nucleic acid analogue sequence may be employed to fence off all that part of the nucleic acid which lies 3' or 5' respectively to the nucleic acid analogue.

Where an endonuclease is employed as the attacking reagent, a short stretch of nucleic acid exposed unhybridised between two nucleic acid analogue oligomers lying adjacent one another on the nucleic acid may none the less form part of the selected region which is protected, by virtue of some interaction between the end bases of the two nucleic acid analogue sequences or because of interference by the nucleic acid analogue with the activity of the endonuclease.

The nucleic acid analogue is preferably one comprising a polymeric strand which includes a sequence of ligands bound to a backbone made up of linked backbone moieties, which analogue is capable of hybridisation to a nucleic acid of complementary sequence.

Said nucleic acid analogue backbone is preferably a polyamide, polythioamide, polysulphinamide or polysulphonamide backbone.

Preferably, said linked backbone moieties are peptide bonded amino acid moieties.

The nucleic acid analogue is preferably capable of hybridising to a nucleic acid of complementary sequence to form a hybrid which is more stable against denaturation by heat than a hybrid between the conventional deoxyribonucleotide corresponding in sequence to said analogue and said nucleic acid.

Preferably, said nucleic acid analogue is a peptide nucleic acid in which said backbone is a polyamide backbone, each said ligand being bonded directly or indirectly to an aza nitrogen atom in said backbone, and said ligand bearing nitrogen atoms mainly being separated from one another in said backbone by from 4 to 8 intervening atoms.

Preferably also, nucleic acid analogue is capable of hybridising to a double stranded nucleic acid in which one strand has a sequence complementary to said analogue, in such a way as to displace the other strand from said one strand.

Preferably, the nucleic acid analogue has the general formula 1:

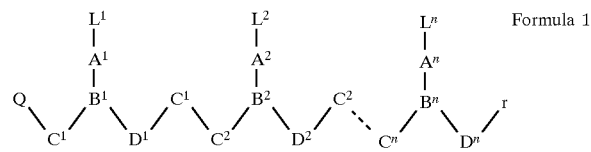

wherein:
n is at least 2,
each of $L^1$–$L^n$ is independently selected from the group consisting of hydrogen, hydroxy, $(C_1$–$C_4)$alkanoyl, naturally occurring nucleobases, non-naturally occurring nucleobases, aromatic moieties, DNA intercalators, nucleobase-binding groups, heterocyclic moieties, and reporter ligands, but normally at least one L will be a nucleobase binding group such as a naturally occurring nucleobase and preferably at least 90% of the groups L will be such nucleobase binding groups;

each of $C^1$–$C^n$ is $(CR^6R^7)_y$, where $R^6$ is hydrogen and $R^7$ is selected from the group consisting of the side chains of naturally occurring alpha amino acids, or $R^6$ and $R^7$ are independently selected from the group consisting of hydrogen, $(C_2$–$C_6)$alkyl, aryl, aralkyl, heteroaryl, hydroxy, $(C_1$–$C_6)$alkoxy, $(C_1$–$C_6)$alkylthio, $NR^3R^4$ and $SR^5$, where $R^3$ and $R^4$ are as defined below, and $R^5$ is hydrogen, $(C_1$–$C_6)$alkyl, hydroxy, alkoxy, or alkylthio-substituted $(C_1$ to $C_6)$alkyl or $R^6$ and $R^7$ taken together complete an alicyclis or heterocyclic system;

each of $D^1$–$D^n$ is $(CR^6R^7)_z$ where $R^6$ and $R^7$ are as defined above;

each of y and z is zero or an integer from 1 to 10, the sum y+z being from 2 to 10 (preferably being more than 2, and most preferably each of y and z being or 1 or 2;

each of $G^1$–$G^{n-1}$ is —$NR^3CO$—, —$NR^3CS$, —$NR^3SO$— or —$NR^3SO_2$—, in either orientation, where $R^3$ is as defined below;

each of $A^1$–$A^n$ $B^1$–$B^n$ are selected such that:
(a) A is a group or formula (IIa), (IIb), (IIc) or (IId), and B is N or $R^3N^+$; or
(b) A is a group of formula (IId) and B is CH;

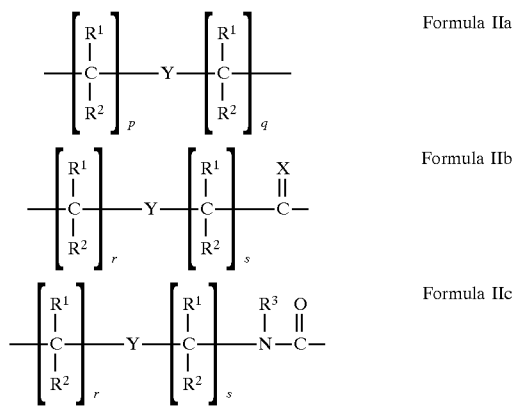

Formula IIa

Formula IIb

Formula IIc

Formula IId wherein:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1$–$C_4)$alkyl which may be hydroxy- or alkoxy- or alkylthio-substituted, hydroxy, alkoxy, alkylthio, amino and halogen; and each $R^3$ and $R^4$ is independently selected from the group consisting of hydrogen, $(c_1$–$C_4)$alkyl, hydroxy- or alkoxy- or alkylthio-substituted $(C_1$–$C_4)$alkyl, hydroxy, alkoxy, alkylthio and amino;

Q is —$CO_2H$, —$CONR'R''$, —$SO_3H$ or —$SO_2NR'R''$ or an activated derivative of —$CO_2H$ or —$SO_3H$; and I is —$NR'R''$, where R' and R'' are independently selected from the group consisting of hydrogen, alkyl, amino protecting groups, reporter ligands, intercalators, chelators, peptides, proteins, carbohydrates, lipids, stercids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers.

More preferably, said nucleic acid analogue comprises a compound of the general formula III, IV or V:

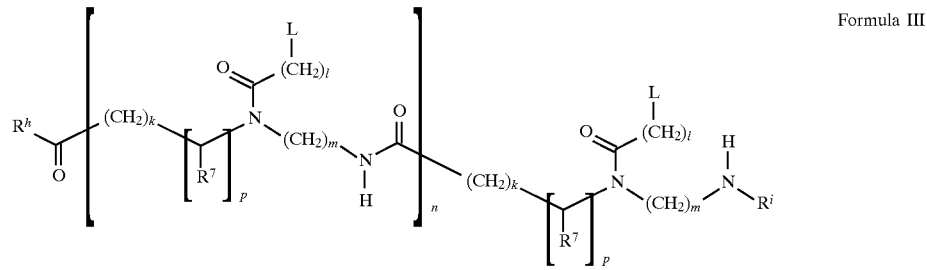

Formula III

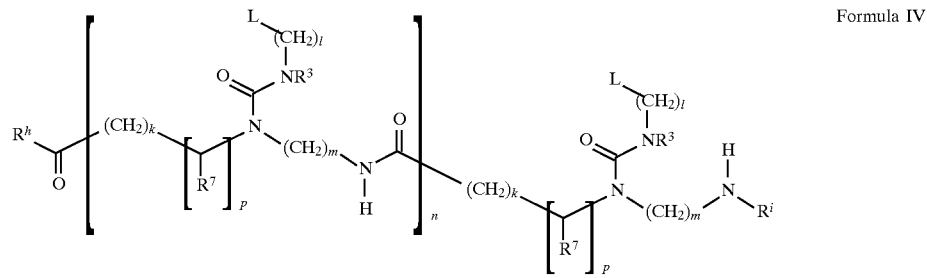

Formula IV

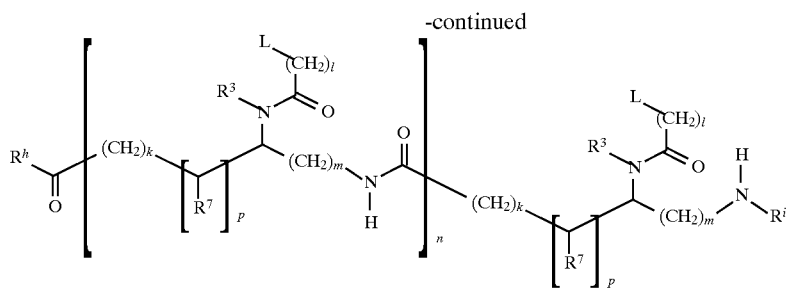

Formula V wherein:

each L is independently selected from the group consisting of hydrogen, phenyl, heterocyclic moieties, naturally-occurring nucleobases, and non-naturally occurring nucleobases;

each $R^7$ is independently selected from the group consisting of hydrogen and the side chains of naturally occurring alpha amino acids;

n is an integer greater than 1, each k, l, and m is, independently, zero or an integer from 1 to 5;

each p is zero or 1;

$R^h$ is OH, $NH_2$ or —$NHLysNH_2$; and $R^i$ is H or —$COCH_3$.

The method of protecting a nucleic acid described above can be used in a method of detecting a nucleic acid sequence. Thus the present invention includes in a second aspect a method of detecting the presence in a nucleic acid sample of a sequence, which method comprises exposing the sample of nucleic acid to a nucleic acid analogue capable of hybridising in sequence selective manner to said sequence if present in said nucleic acid sample under hybridising conditions so as to form a complex between said nucleic acid analogue and a region of said nucleic acid containing said sequence, exposing said nucleic acid to a reagent capable of degrading said nucleic acid under conditions such that the said region of said nucleic acid forming said complex is protected from attack by said reagent whilst the remainder of said nucleic acid is degraded, and detecting the presence of said complex.

There will be many ways of detecting the presence of said complex. These may be divided into those which detect the complex as such and those in which the complex is broken up into its constituents of nucleic acid and nucleic acid analogue and the presence of the nucleic acid or the nucleic acid analogue is detected. The existence of the complex can be deduced from the survival of the nucleic acid.

In the first group of methods, reliance may be placed upon differences in properties of the nucleic acid analogue and the nucleic acid/nucleic acid analogue hybrid. Thus preferably, the presence of said complex is detected by comparing the movement of said complex in electrophoresis with the movement of said nucleic acid analogue under similar conditions.

Preferably, the nucleic acid analogue or the nucleic acid carries a detectable label, suitable labels for the nucleic acid analogue include a fluorescent label. a radio-label, an enzyme label, biotin, a spin label, a chemiluminescent label, an antigen label or an antibody label. The most preferred of these are the use of a fluorophore or a radioisotope as a label but generally any method of labelling applicable to peptides can be used.

In a preferred practice of the second aspect of the invention, the nucleic acid analogue is a labelled nucleic acid analogue produced by a method for labelling a nucleic acid analogue comprising providing a nucleic acid analogue with a peptide motif capable of functioning as a substrate for an enzyme in a labelling reaction and carrying out a said labelling reaction comprising reacting the peptide motif of the nucleic acid analogue under the influence of an enzyme with a source of said label.

Preferably, said label is a radio-label.

The source of said label is preferably radio-labelled ATP.

Said enzyme is preferably a protein kinase.

The peptide motif is preferably the kemptide motif.

Preferably, the labelling reaction is a phosphorylation at a serine residue of said peptide motif.

An alternative method of labelling a nucleic acid analogue involves providing, preferably at one end of the nucleic acid analogue, a chelating moiety capable of binding at least one metal ion by chelation and chelating a radioisotope or fluorophore directly or indirectly thereto. For instance, a europium ion may be chelated by a suitable chelating moiety carried by the nucleic acid analogue to act as a fluorescent label.

An alternative detection method in this first group makes use of the nucleic acid sequence which is protected to act as a means of linking two nucleic acid analogue sequences which would otherwise not associate. If each bears a different type of label, the association of the two labels can be detected. By way of example, two nucleic acid analogue oligomers may be hybridised to respective ends of a target nucleic acid sequence forming part of a larger nucleic acid sequence. One nucleic acid analogue is labelled with a moiety suitable for linking to a solid phase e.g. a chelating peptide motif such as $His_5$. The other is provided with a detectable label, e.g. is radio-labelled. After digestion of unprotected nucleic acid, the two nucleic acid analogue sequences are left joined via hybridisation to the target nucleic acid protected sequence. The complex may be captured on a solid support bearing chelatable nickel ions via chelation by the first nucleic acid analogue. Radio-labelled excess second nucleic acid analogue may be washed away and the radio activity of the second labelled nucleic acid analogue may be detected on the solid support or after elution from it.

Other examples would include having one nucleic acid analogue bearing biotin as a moiety suitable for linking to a solid phase instead of the chelating peptide motif and the second nucleic acid analogue linked to a detectable label, e.g. an enzyme or a fluorophore. If the detectable label is an enzyme capable of catalysing the production of a detectable product, the assay is analogous to the well established ELISA principle in immunoassay.

Alternative means for separating hybridised from non-hybridised nucleic acid analogue include reverse phase or ion exchange chromatography, or gel filtration. An antibody selection procedure could be used employing an antibody with specificity for intact nucleic acid or with specificity for the nucleic acid/nucleic acid analogue hybrid.

In the second group of detection methods, the complex between the nucleic acid and the nucleic acid analogue is denatured and the survival of the protected nucleic acid sequence is demonstrated, suitably by known nucleic acid sequence detection methods such as a hybridisation assay. Optionally, the nucleic acid sequence may be subjected to an amplification procedure. LCR will generally be preferred for amplifying short protected sequences and PCR for longer ones.

Nucleic acid amplification procedures, especially the well known PCR procedures often encounter difficulties when the target sequence to be amplified is present amongst a large amount of other nucleic acid.

As is shown above, the present invention provides a ready means of "cleaning up" a nucleic acid sample by degrading all nucleic acid present except the target sequence, thus allowing amplification to be more easily carried out whether for the purposes of assay or preparatively.

Accordingly, the present invention provides in a third aspect, a method of carrying out a nucleic acid amplification comprising protecting a selected region of a nucleic acid within a nucleic acid sample by hybridising to said nucleic acid a nucleic acid analogue which hybridises thereto in a sequence specific manner, exposing said sample to a nucleic acid attacking reagent to degrade the nucleic acid in the sample except for said selected region, and amplifying said selected region.

To free the protected sequence amplification, the nucleic acid/nucleic acid analogue hybrid may be denatured by heat. Any amplification method may be employed, including all presently known method such as PCR and its variants, LCR and 3SR.

In WO 93/25706 (PCT/EP93/01435) a method is described for sterilising a nucleic acid amplification by hybridising to the amplification product a nucleic acid analogue which will prevent any amplification from acting as an amplifiable target. This may be still further improved according to a fourth aspect of the present invention by protecting a region of the amplification product which excludes at least one primer binding site necessary for repetition of the amplification by a method in accordance with the first aspect of the invention, degrading the remaining nucleic acid, including the primer binding sites of the amplification product, and detecting the survival of the protected nucleic acid as discussed above. Preferably, at least some, more preferably the whole, of all the primer binding sequences are degraded.

The nucleic acid analogue may be present throughout a PCR procedure, provided that the temperatures employed are high enough to melt the nucleic acid analogue off the nucleic acid, or may be added at the end of the amplification. The attacking reagent will need to be added following the amplification but may be added from a separate compartment within a closed amplification apparatus so that amplified product never has an opportunity to escape and become a contaminant.

The invention will be illustrated by the following examples with reference to the accompanying drawings in which:

FIG. 1 is an autoradiograph of gel showing the results of Examples 3 to 5.

One convenient method of producing a PNA bearing a radio-label of high specific activity particularly preferred for use in the present invention is described in our co-pending British patent application No. 9324956.3 (bearing agent's reference P3685GB), filed on the same day as this application. According to such a method in its preferred form, a PNA is prepared having a teminal kemptide extension which undergoes a reaction with $^{32}p$ ATP mediated by protein kinase A to acquire a $^{32}p$ label bound to a serine residue. PNA's having peptide extensions of desired amino acid sequences can conveniently be produced by the Boc or Fmoc solid phase techniques well understood in the art once a starting PNA sequence has been built-up on the solid support suitable by using the Boc solid phase synthesis described in WO 92/20703.

According to preferred forms of the first aspect of the present invention, a nucleic acid containing sequences to be protected may be treated with a PNA having a sequence complementary to the sequence of interest. If the nucleic acid is DNA, it may be in double stranded form and one may rely on the ability of the nucleic acid analogue to hybridise to its target sequence in double stranded form. However, it may be necessary and will normally be desirable to denature the double stranded target DNA, usually by heating. The DNA may be quite impure, i.e. other cell products may be present. Also, the DNA may be whole genomic DNA or total cell RNA extracted from cells and not digested into shorter lengths. The DNA or RNA could also be the product of a nucleic acid amplification procedure such as LCR or PCR or a NASBA (3SR) amplification. Preferred PNA's will bind sequence selectively with high affinity, even if the target DNA is double stranded. The nucleic acid sample may then be treated with a nuclease or nuclease mixture to degrade all of the nucleic acid not protected by hybridisation to the PNA. The PNA may be present in substantial excess to ensure that if there is even one correct sequence present in the nucleic acid sample, it will be hybridised and protected.

The reaction product may be subjected to electro-phoresis on a gel or in a capillary to separate PNA which is hybridised to nucleic acid from non-hybridised PNA. Because PNA is an essentially neutral molecule, having one positive charge per molecule typically at a terminal amine group, it shows little tendency to migrate during electrophoresis. Nucleic acids on the other hand are highly negatively charged and hybridisation of PNA to a nucleic acid fragment results in a negatively charged hybrid which will migrate under electrophoresis in the opposite direction to the PNA itself. This effects a ready and highly specific separation of the hybridised and non-hybridised PNA. If the PNA is appropriately labelled, it is possible to detect extremely small quantities of it and the analytical method according to the second aspect of the invention provides an excellent signal to noise ratio.

PNA's are able to distinguish nucleic acid sequences differing by only one residue. Accordingly, the methods described above offer the possibility of a very quick and simple assay capable of determining whether a sample of genomic DNA contains a particular allelic variation within a particular gene. Furthermore, as PNA's of different lengths hybridised to nucleic acids are readily separable under electrophoresis, the possibility also exists of probing a nucleic acid sample with a plurality of PNA's simultaneously, digesting away all the unhybridised nucleic acid and by electrophoresis separating all the PNA/nucleic acid hybrids from the unhybridised excess PNA'S and from each other. One may thus in a single assay demonstrate that a DNA sample contains, possibly on different genes, some particular combination of allelic variations of interest, eg. one found to give rise to a particular phenotype such as a disease state.eb;normal

BRIEF DESCRIPTION OF THE DRAWINGS

FIG. 1 is an autoradiograph of a gel showing the results of Examples 3 to 5.

EXAMPLE 1

Preparation of a PNA-kemptide Chimera

The solid phase PNA synthesis described in WO 92/20703 was used to build up sequence: A(Z).C(Z)TA(Z)-CONH-resin SEQ. I.D. NO. 1.

The N terminal Boc group was removed by treatment with TFA and used as a starting point for a standard boc type solid phase peptide synthesis of the kemptide motif via the linker 6-amino-hexanoic acid to produce the chimera:

Boc-Leu-Arg(Tos)-Arg(Tos)-Ala-Ser-(Bzl)-Leu-Gly-NH$(CH_2)_5$CONH[SEQ. ID NO:2]TG(Z)T.A(Z)C(Z)G(Z.TC(Z) A(Z).C(Z)A(Z) A(Z).C(Z)TA(Z) —CONH-resin [SEQ ID NO.1]

The protection groups were removed and the product cleaved from the resin by Low-High TFMSA procedure. The raw product was purified by preparative HPLC (reversed phase $C_{18}$ eluting with a gradient of A:0.1% TFA in water (MilliQ.™) and B:0.% TFA, 10% water,90% acetonitrile) . The purified chimeric PNL-kemptide was characterized by analytical HPLC and FAB-MS.

EXAMPLE 2

Radio Labelling of the Kemptide Motif (Leu-Arg-Arg-Ala-Ser-Leu-Gly) By Protein Kinase A The PNA-kemptide chimera of the formula:

H - L e u - A r g - A r g - A l a - S e r - L e u - G l y - TGTACGTCACAACTA-NH2 [SEQ. I.D. NO.2] was labelled with $^{32}p$ in a reaction mixture containing:

| | |
|---|---|
| PNA-kemptide, 10 μM | 5 μl |
| 10 × Protein Kinase A buffer | 5 μl |
| γ $^{32}$P ATP (>5000 Ci/mmol; 50 μCi/μl) | 10 μl |
| Protein kinase A (Boehringer; 5 mU/μl) | 0.2 μl |
| H$_2$O | 30 μl |

The reaction was incubated for 30 minutes at 30° C. and then for 10 minutes at 65° C. before being centrifuged for 30 seconds at 15000 g. The supernatant was transferred to a new eppendorff tube. Water was added to 1 ml and the labelled PNA-kemptide was separated from unincorporated γ$^{32}$p ATP by anion exchange chromatography using a DEAE Sephadex A 50™ anion exchange column.

The specific activity of the PNA-kemptide was estimated at 1×10$^8$ cpm/μg PNA-kemptide.

EXAMPLE 3

Detection of DNA sequence via protection by PNA.

The 15-mer PNA bearing the radio-labelled kemptide motif as made in Example 2 was incubated for 15 minutes separately with each of the following nucleic acids:

1. None (See FIG. 1 lane 1)

2. Complementary DNA 15-mer. (See FIG. 1 lanes 2 and 5)

3. DNA 10-mer complementary to part of the sequence of the PNA. (See FIG. 1 lane 3)

4. DNA 40-mer 5'CTAGAGGATCTAGTTGTGAC-GTACAGGATCTTTTTCATAG- 3[SEQ. ID NO. 3] containing a 15 base sequence complementary to the PNA in the centre of the sequence. (See FIG. 1 lanes 4 and 6)

In each case, 4 μl of a 10 μM solution of the oligonucleotide was mixed with 5 μl of the labelled PNA in a 10 μl reaction volume containing 30 mM NaAc (pH 5.0), 50 mM NaCl, 10 mM ZnCl$_2$ and 55 %v/v glycerol. Incubation for 15 minutes took place at room temperature.

In the case of one out of two reactions using the 40-mer DNA and in case of one out of two reactions using the 15-mer DNA, 15 units of mung bean nuclease were added and the reactions were incubated at 37° C. for 5 minutes.

All reactions were terminated by adding 10 μl of loading buffer (30% v/v glycerol, 0.25% w/v bromophenol blue, 0.25% xylene cyanol, 0.01% SDS) and the reaction mixtures were subjected to electrophoresis in a 10% polyacrylamide gel and subsequently to autoradiography.

The results are shown in FIG. 1 lanes 1 to 6. In lane 1 the labelled PNA is run alone and nothing is seen because it is immobile on the gel. In lane 2 the labelled PNA is hybridised to the 15-mer DNA and a band is seen for the hybrid. In lane 3 the labelled PNA is hyridised to the 10-mer DNA and it can be seen that the band produced is clearly distinguishable from that in lane 2 in the distance run on account of the difference in the size of the two oligo-DNA's involved. In lane 4 the PNA is hybridized to the 40-mer DNA and once again the distance run by the baud on the gel allows one to discriminate between the $^{15}$PNA/$^{10}$DNA and $^{15}$PNA/$^{15}$DNA hybrids and the $^{15}$PNA/$^{40}$DNA hybrid.

In lane 5 one sees the result of nuclease digestion in the case of the $^{15}$PNA/$^{15}$DNA hybrid. The band is the same as that in lane 2 showing that the nuclease has been unable to degrade the hybridised DNA. Lane 6 shows the result of the nuclease digestion of the $^{15\ PNA/40}$DNA hybrid. Once again, the band is as in lane 2, showing that only that part of the DNA which is hybridised to the PNA is protected against the nuclease. The internal 15-mer sequence in the 40-mer DNA which is complementary to the PNA has therefore been detected by the procedure described above with reference to lane 6.

EXAMPLE 4

Protection of RNA against nuclease by PNA.

PNA $T_{10}$ bearing the kemptide motif was labelled as in Example 2. The labelled PNA was incubated with a mixture of polyadenylated RNA's according to the following procedure. PNA (5 μl) was incubated with 4 μl of 100ng/μl mixed in vitro RNA transcripts (Gibco BRL) in a 10 μl reaction volume containing other constituents and under time and temperature conditions as in Example 3. A similar incubated mixture was further incubated with mung bean nuclease as in Example 3 and the reaction mixtures were prepared for and subjected to electrophoresis and autoradiographed as in Example 3. The results are seen in lanes 7 and 8 of FIG. 1.

Lane 7 shows an unresolved ladder of different sizes of PNA/RNA hybrids. In lane 8, the nuclease has resolved the ladder into a single band by trimming off all the RNA's to the $A_{10}$ portion protected by the PNA.

EXAMPLE 5

Detection of single base pair variation in 15-mer DNA

The 15-mer labelled PNA used in Example 3 was hybridized to two different DNA's under both of two different temperature conditions as follows.

The labelled PNA was hybridised to complementary 15-mer DNA at incubation temperatures of 55° C. and 65° C. respectively and in each case the reaction mixture was treated at that temperature with mung bean nuclease. In other respects the conditions were as in Example 3. Two similar incubations took place using the single base mismatched 15-mer DNA 5'-TAGTTGCGACGTACA[SEQ. ID NO.4 ]- 3' at the same two temperatures with subsequent addition of mung bean nuclease. The resulting autoradiographs are seen in lanes 9 to 12 of FIG. 1.

In lane 9 the result of the hybridization of the PNA to its fully complementary DNA at 65° C. with nuclease degradation is a band corresponding to protection of the DNA by the PNA. Lane 10 shows the result of hybridisation at 65° C. with the single base mismatch. The DNA is not protected and no hybrid is seen. Lane 11 shows the result of the experiment at 55° C. with the fully complementary sequence and lane 12 shows the result of the 55° C. experiment with the single mismatch. In both these lanes the protected DNA is detected.

The melting point for the perfectly matched 15-mer hybrid is 69° C. Under the stringent hybridisation conditions imposed by operating close to this melting point, the PNA distinguishes between the perfectly matched DNA and the single base mismatch for which the melting point is 61° C. At 55° C. however, hybrids are formed both with the perfect match and the single base mismatch as would be predicted from the melting points of the hybrids.

In the above description, alkyl moieties, unless otherwise specified, preferably contain 1–6, most preferred 1–3 carbon atoms. Aromatic moieties, preferably 6–14, most preferred 6–10 carbon atoms. Both alkyl moieties and aromatic moieties may be substituted or unsubstituted by groups containing heteroatoms, such as O, N or S. The alkyl moieties can be straight-chained or branched.

Preferred aromatic moieties are phenyl, imidazolyl, or pyridyl. Preferred DNA intercalators include anthraquinolyl, psoralyl or ethidium bromide.

Preferred heterocyclic moieties include piperidinyl, morpholinyl or pyrrolidinyl.

Preferred reporter ligands include biotinoyl, dioxigenoyl or fluoresceinoyl.

Preferred chealting moieties include EDTA, NTA or bispyridinoyl.

Preferred aryl groups are phenyl. Preferred aralkyl groups are tolyl. Preferred heteroaryl groups include pyrimidinyl.

Preferred alicyclic or heterocyclic groups for $R^6$ and $R^7$ include cyclohexenoyl and piperazinoyl.

Examples of groups for R' and R" are the following:

alkyl: methyl; an amino protecting group: butyloxycarbonyl; a reporter ligand: biotin; an intercalator: anthraquinolyl; a chelator: bispyridyl; a peptide: kemptide; a protein: alkaline phosphatase; a carbohydrate: sucrose; a lipid: cholesterol; a steroid: dioxigenin; a nucleoside: adenosin; a nucleotide: adenosine monophosphate; a nucleotide diphosphate: adenosine diphosphate; a nucleotide triphosphate: adenosine triphosphate; an oligonucleotide: $A_{10}$; a soluble polymer: dextrane; a non-soluble polymer: magnetic bead.

We claim:

1. A method for detecting a specific nucleic acid sequence contained in a nucleic acid sample, comprising
    (a) hybridizing at least one nucleic acid analogue with the 5'-end of a nucleic acid sequence to be detected in a reaction mixture, to form a complex which protects the nucleic acid sequence from degradation by a degrading reagent which is capable of degrading the nucleic acid from the 5'-end thereof,
    (b) adding a degrading reagent to said reaction mixture thereby exposing said complex to said degrading reagent without degradation of the specific nucleic acid sequence due to the formation of the complex; and thereafter
    (c) detecting the complex or said specific nucleic acid sequence.

2. The method according to claim 1, further comprising, before step (a), combining the nucleic acid sample with an excess amount of the at least one nucleic acid analogue, compared to the nucleic acid sample, and
    after step (b), separating the complex and any non-hybridized nucleic acid analogue.

3. The method of claim 1, wherein the detecting step (c) comprises denaturing the complex and thereafter detecting the nucleic acid sequence.

4. The method of claim 3, wherein the nucleic acid sequence is detected via a hybridization assay.

5. The method of claim 3, further comprising, after the denaturing step amplifying the nucleic acid sequence.

6. The method of claim 1, wherein the nucleic acid analogue and the nucleic acid sample form a complex which is more stable against heat denaturation than a complex between a conventional DNA, corresponding in sequence to the nucleic acid analogue, and the nucleic acid sample.

7. The method of claim 1, wherein the nucleic acid analogue comprises a polymeric strand portion comprising
    (a) a backbone comprising a plurality of linked backbone moieties; and
    (b) a plurality of ligands, each of the ligands being bound to at least one of the liked backbone moieties.

8. The method of claim 7, wherein the backbone comprises polyamide, each of the ligands is bound directly or indirectly to an aza nitrogen atom in the backbone, and wherein each ligand-binding aza nitrogen atom is separated from an adjacent ligand-binding aza nitrogen atom by from 4 to 8 intervening atoms in the backbone.

9. The method of claim 1, wherein the nucleic acid sample is double-stranded and the nucleic acid analogue hybridizes to a first strand of the double-stranded nucleic acid sample to displace a second strand of the double-stranded nucleic acid sample from the first strand.

10. A method for detecting a specific nucleic acid sequence contained in a nucleic acid sample, comprising
    (a) hybridizing at least one nucleic acid analogue with the nucleic acid at the 3'-end of said specific nucleic acid sequence to be detected in a reaction mixture, to form a complex which protects the specific nucleic acid sequence from degradation by a degrading reagent which is capable of degrading the nucleic acid from the 3'-end thereof,
    (b) adding a degrading reagent to said reaction mixture thereby exposing said complex to said degrading reagent without degradation of the specific nucleic acid sequence due to the formation of the complex; and thereafter
    (c) detecting the complex or the specific nucleic acid sequence.

11. The method according to claim 10, further comprising, before step (a), combining the nucleic acid sample with an excess amount of the at least one nucleic acid analogue, compared to the nucleic acid sample, and after step (b), separating the complex and any non-hybridized nucleic acid analogue.

12. The method of claim 10, wherein the detecting step (c) comprises denaturing the complex and thereafter detecting the nucleic acid sequence.

13. The method of claim 12, wherein the nucleic acid sequence is detected via a hybridization assay.

14. The method of claim 12, further comprising, after the denaturing step, amplifying the nucleic acid sequence.

15. The method of claim 10, wherein the nucleic aced analogue and the nucleic acid sample form a complex which is more stable against heat denaturation than a complex between a conventional DNA, corresponding in sequence to the nucleic acid analogue, and the nucleic acid sample.

16. The method of claim 10, wherein the nucleic acid analogue comprises a polymeric strand portion comprising (a) a backbone comprising a plurality of linked backbone moieties; and (b) a plurality of ligands, each of the ligands beings bound to at least one of the linked backbone moieties.

17. The method of claim 16, wherein the backbone comprises polyamide, each of the ligands is bound directly or indirectly to an aza nitrogen atom in the backbone, and wherein each ligand-binding aza nitrogen atom is separated from an adjacent ligand-binding aza nitrogen atom by from 4 to 8 intervening atoms in the backbone.

18. The method of claim 10, wherein the nucleic acid sample is double-stranded and the nucleic acid analogue hybridizes to a first strand of the double-stranded nucleic acid sample to displace a second strand of the double-stranded sample from the first strand.

19. A method of detecting a specific nucleic acid sequence contained in a nucleic acid sample, comprising (a) hybridizing at least two nucleic acid analogues with a nucleic acid in a reaction mixture to form a complex which protects a specific nucleic acid sequence from degradation by a degrading reagent which is capable of degrading the nucleic acid in the absence of said nucleic acid analogues, (b) adding the degrading reagent to the reaction mixture thereby exposing said complex to said degrading reagent without degradation of the specific nucleic acid sequence due to the formation of the complex, and thereafter (c) detecting the complex or the specific nucleic acid sequence.

20. The method of claim 19, wherein in the hybridizing step (a), the nucleic acid sample hybridizes with a first nucleic acid analogue at least a first end of the nucleic acid sequence to be detected, and the nucleic acid sample hybridizes with a second nucleic acid analogue at at least a second end of the nucleic acid sequence to be detected.

21. The method of claim 20, wherein the first nucleic acid analogue comprises a moiety capable of linking to a solid phase, and the second nucleic acid analogue comprises a detectable label, and wherein the detecting step (c) comprises linking the moiety to the solid phase and thereafter detecting the detecting the detectable label.

22. A method for detecting a specific nucleic acid sequence contained in a nucleic acid sample, comprising (a) hybridizing at least one nucleic acid analogue with the nucleic acid at said specific nucleic acid sequence in a reaction mixture, to form a complex which protects the nucleic acid from degradation by a degrading reagent which is capable of degrading all nucleic acids not hybridized to said nucleic acid analogue;

(b) adding the degrading reagent to said reaction mixture thereby exposing said complex to said degrading reagent without degradation of the nucleic acid analogue; due to the formation of the complex; and thereafter (c) detecting the complex or the specific nucleic acid sequence.

23. A method of amplifying a specific nucleic acid sequence contained in a nucleic acid sample, comprising (a) hybridizing at least one nucleic acid analogue with the nucleic acid, to form a complex which protects the specific nucleic acid sequence from a degrading reagent which is capable of degrading the nucleic acid in the absence of the nucleic acid analogue;

(b) exposing the complex to the degrading reagent without degradation of the nucleic acid sequence due to the formation of the complex; and thereafter (c) amplifying the specific nucleic acid sequence.

* * * * *

UNITED STATES PATENT AND TRADEMARK OFFICE
CERTIFICATE OF CORRECTION

PATENT NO. : 5,861,250

DATED : January 19, 1999

INVENTOR(S) : Stanley et al.

It is certified that error appears in the above-identified patent and that said Letters Patent is hereby corrected as shown below:

On the title page, insert item [62] :

-- Related U. S. Application Data

[62] Continuation-in-part of International Application PCT/EP94/03973, 11/30/94. --

Signed and Sealed this

Twenty-ninth Day of June, 1999

Attest:

Q. TODD DICKINSON

*Attesting Officer*     Acting Commissioner of Patents and Trademarks

UNITED STATES PATENT AND TRADEMARK OFFICE
CERTIFICATE OF CORRECTION

PATENT NO. : 5,861,250
DATED : January 19, 1999
INVENTOR(S) : Stanley et al.

It is certified that error appears in the above-identified patent and that said Letters Patent is hereby corrected as shown below:

On the title page

Insert Item [30],

-- [30] Foreign Application Priority Data

Dec. 06, 1993   [GB]   Great Britain..............9324955.5 --

Signed and Sealed this

Fourteenth Day of September, 1999

Attest:

Q. TODD DICKINSON

*Attesting Officer*      *Acting Commissioner of Patents and Trademarks*